United States Patent [19]
Yasuda et al.

[11] Patent Number: 5,543,288
[45] Date of Patent: Aug. 6, 1996

[54] SURFACE-ACTIVE COMPOUND AND A SILVER HALIDE PHOTOGRAPHIC MATERIAL CONTAINING THE SAME

[75] Inventors: Tomokazu Yasuda; Yukio Karino; Masatoshi Nakanishi, all of Minami-ashigara, Japan

[73] Assignee: Fuji Photo Film Co., Ltd., Kanagawa, Japan

[21] Appl. No.: 288,609

[22] Filed: Aug. 10, 1994

[30] Foreign Application Priority Data

Aug. 18, 1993 [JP] Japan .................................... 5-204325

[51] Int. Cl.$^6$ .................................................. G03C 1/38
[52] U.S. Cl. ...................... 430/631; 430/601; 430/610; 430/634; 430/635; 430/636
[58] Field of Search ................................ 430/631, 601, 430/634, 635, 636, 610

[56] References Cited

U.S. PATENT DOCUMENTS 4,367,283  4/1983  Nakayama et al. ................ 430/631

FOREIGN PATENT DOCUMENTS 1932299  1/1971  Germany.
1288434  9/1972  United Kingdom.

Primary Examiner—Thorl Chea
Attorney, Agent, or Firm—Sughrue, Mion, Zinn, Macpeak & Seas

[57] ABSTRACT

There is disclosed a novel surface-active compound, and a silver halide photographic material and a processing solution for a silver halide photographic material containing the same. The surface-active compound is represented by the following formula (I):

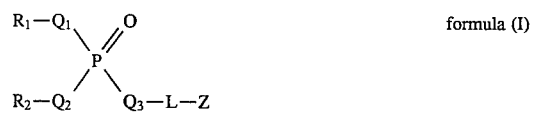

formula (I)

Wherein $R^1$ represents an aliphatic group, an alicyclic compound group, an aromatic group, or a heterocyclic ring; $R^2$ represents an aliphatic group, an alicyclic compound group, an aromatic group, a heterocyclic ring, or a group represented by —L—Z; $Q^1$, $Q^2$, and $Q^3$ each represent a single bond, an oxygen atom, a sulfur atom, or a group represented by —N($R^3$)—, in which $R^3$ represents a hydrogen atom or a group represented by $R^2$; L represents a divalent linking group; and Z represents an ionic group.

13 Claims, No Drawings

SURFACE-ACTIVE COMPOUND AND A SILVER HALIDE PHOTOGRAPHIC MATERIAL CONTAINING THE SAME

FIELD OF THE INVENTION

The present invention relates to a novel surface-active compound, and more particularly to a surface-active agent as a dispersant for hydrophobic organic compounds that is excellent in dispersing ability, emulsifying ability, and dispersion stability.

The present invention relates also to a silver halide photographic material having a dispersion of a specific photographically useful substance in a specific layer, and more particularly to a silver halide photographic material having a hydrophilic colloid layer containing a photographically useful substance that is photochemically inactive during storage, namely that hardly causes the occurrence of fluctuation of photographic properties during storage, and that can exhibit a required reactivity easily when it is photographically processed.

BACKGROUND OF THE INVENTION

Silver halide photographic materials are formed by introducing various photographically useful compounds into hydrophilic colloid layers in order to allow various photographic functions to be exhibited. In that case, in particular, with respect to multi-layer photographic materials, water-insoluble substances are used to hold intended photographically useful substances in particular layers, to allow their functions to be exhibited. These water-insoluble substances are oil-soluble substances in many cases. The water-insoluble substance is formed into fine emulsified particles by stirring it at a high speed, with a dispersing solvent, a dispersing medium, and, if required, a co-solvent (high-boiling organic solvent), in the presence of a surface-active agent, in order to introduce the water-insoluble substance into a hydrophilic colloid layer of a photographic material, followed by coating and drying.

Obtaining a dispersion that is stable during storage and during the coating step and the drying step is required in order to avoid problems, such as nibs; and obtaining or not obtaining finely dispersed grains, influence the photographic properties greatly. For example, it is known that, in dispersing dye-forming couplers (hereinafter abbreviated to couplers), obtaining a fine dispersion can improve reactivity and can attain a high dye-forming efficiency; and, in dispersing a color-mix inhibitor for use in an intermediate layer, obtaining a fine dispersion can secure a high color-mix inhibition activity.

Further, in the case of nucleators, which are water-insoluble photographically useful substances for use, for example, in photographic materials for printing, since the polarity of nucleators is subtle, there are few preferable dispersion techniques. A dispersion is prepared, for example, by mixing a solution of a nucleator in an organic solvent in the presence of large amounts of a surface-active agent and a protective colloid, followed by deposition, which technique involves a problem in view of the stability of the dispersion and the use of a large amount of a surface-active agent.

In the above production of a fine particle dispersion, generally, since the type and the amount of the used surface-active agent cause the size and stability of the obtainable grains to change greatly, the surface-active agent is a great governing factor in the emulsifying and dispersing processes. Therefore, research on surface-active agents that will enable the fine dispersion has hitherto been made, and various emulsion stabilizers useful for photographic systems have been found. Examples of these emulsion stabilizers are described, for example, in JP-A ("JP-A" means unexamined published Japanese patent application) Nos. 129229/1976 and 20251/1985, U.S. Pat. Nos. 3,428,456 and 3,963,688, and West German Patent Application (OLS) Nos. 1,932,299 and 2,123,455. However, there are as yet no surface-active agents that can give stable fine dispersions when they are used in small amounts for a wide variety of compounds. Although use of a large amount of a surface-active agent and use of a water-miscible organic co-solvent can give a fine dispersion, use of a large amount of a surface-active agent results in processing stain and foaming, due to the dissolving out thereof into a photographic processing solution in a processing step and accumulation thereof in the photographic processing solution, often resulting in serious problems. Particularly, in recent years, as the replenishment rate of processing solutions has been made low, even the conventional amount of surface-active agents to be used sometimes causes a problem. Further, since the use of a water-miscible organic solvent is accompanied by the generation of organic solvent gas when the dispersion is produced, a serious problem occurs in view of the need for counterplan equipment for the recovering process and the deterioration of the production environment.

Therefore, development of a surface-active agent that, when used in a small amount for a wide variety of compounds, can give stably a fine dispersion, is desired.

As described above, in producing a fine dispersion for photographic materials, high-boiling organic solvents are often used. If a dispersion is prepared without using these high-boiling organic solvents, particles of the dispersion are difficult to be made fine stably. In addition, problems often arise, i.e., the photographic properties of the photographic material coated with the dispersion are damaged (e.g., the sensitivity is lowered, the color-forming property is lowered, or fine crystals deposit), which is a very great hindrance to the designing of photographic materials. On the other hand, however, injurious effects occur due to the use of high-boiling organic solvents. For example, it is well known that when a dye-forming coupler is used as an oil-soluble photographically useful substance, stain occurs on the surface of the photographic material, due to exudation of the high-boiling organic solvent with the lapse of time during storage of the photographic material. Further, an increase in the film thickness of the photographic material, resulting from an increase in a hydrophilic colloid used to compensate for softening of the film, caused by the introduction of the oil-soluble component; and lowering of the color-forming property, due to lowering of the reactivity of a coupler, caused by crystallization of the coupler, cause serious problems.

Therefore, development of a technique capable of preparing a fine dispersion without damaging the reactivity of the dispersed oil-soluble photographically useful compound, and without using a high-boiling organic solvent, is desired.

The above dispersion prepared for photographic materials is stored in a refrigerator or at ordinary temperatures, according to requirement, after the preparation and before the production of the photographic material. At that time, the proceeding of deterioration of the dispersion with the lapse of time, such as separation of oil components and crystallization, often causes a serious problem. In this case, since the stability after the lapse of time changes due to the type and amount of the surface-active agent used, development of a surface-active agent that is excellent in stability during storage of the dispersion is desired.

SUMMARY OF THE INVENTION

The first object of the present invention is to provide a novel surface-active compound that, when used in a small amount, can give fine dispersion particles stably.

The second object of the present invention is to provide a silver halide photographic material containing a dispersion of fine particles of a photographically useful compound that is excellent in production suitability.

The third object of the present invention is to provide a silver halide photographic material containing a dispersion of fine particles of a photographically useful compound that is excellent in reactivity in the processing steps, by fixing the photographically useful compound in a particular layer selectively, without adversely influencing the reactivity of the photographically useful compound in the film and the film quality.

The fourth object of the present invention is to provide a silver halide photographic material containing a fine dispersion of a photographically useful compound that is free from stain and foaming when the photographic material is processed.

The above and other objects, features, and advantages of the invention will become fully apparent in the following description.

DETAILED DESCRIPTION OF THE INVENTION

The inventors of the present invention have studied keenly and have found that the above objects can be attained by providing:

(1) A silver halide photographic material, which comprises a surface-active compound represented by the following formula (I):

formula (I)

wherein $R_1$ represents an aliphatic group, an alicyclic compound group, an aromatic group, or a heterocyclic ring; $R_2$ represents an aliphatic group, an alicyclic compound group, an aromatic group, a heterocyclic ring, or a group represented by —L—Z; $Q_1$, $Q_2$, and $Q_3$ each represent a single bond, an oxygen atom, a sulfur atom, or a group represented by —N($R_3$)—, in which $R_3$ represents a hydrogen atom or a group represented by $R_2$; L represents a divalent linking group; and Z represents an ionic group.

(2) A processing solution for a silver halide photographic material, which comprises a compound represented by the formula (I) as stated in (1) above.

(3) A surface-active compound represented by the following formula (II):

formula (II)

wherein $R_1$ represents an aliphatic group, an alicyclic compound group, an aromatic group, or a heterocyclic ring; $R_2$ represents an aliphatic group, an alicyclic compound group, an aromatic group, a heterocyclic ring, or a group represented by —L—Z; $Q_4$, $Q_5$, and $Q_6$ each represent a single bond, an oxygen atom, a sulfur atom, or a group represented by —N($R_3$)—, in which $R_3$ represents a hydrogen atom or a group represented by $R_2$, except that all of $Q_4$, $Q_5$, and $Q_6$ are not oxygen atoms at the same time; L represents a divalent linking group; and Z represents an ionic group.

The present invention is further described in detail.

In formulas (I) and (II), the aliphatic group represented by $R_1$ preferably includes, for example, a straight-chain or branched unsubstituted alkyl group having 1 to 40 carbon atoms (e.g., methyl, ethyl, n-propyl, iso-propyl, n-butyl, sec-butyl, tert-butyl, n-amyl, tert-amyl, n-hexyl, n-heptyl, n-octyl, tert-octyl, 2-ethylhexyl, n-nonyl, 1,1,3-trimethylhexyl, n-decyl, n-dodecyl, cetyl, hexadecyl, 2-hexyldecyl, octadecyl, eicosyl, 2-octyldodecyl, docosyl, tetracosyl, 2-decyltetradecyl, and tricosyl), a straight-chain or branched substituted alkyl group having 1 to 40 carbon atoms (the substituent including, for example, an alkoxyl group, an aryl group, a halogen atom, a carbonester group, a carbonamide group, a carbamoyl group, an oxycarbonyl group, and a phosphate group)(e.g., benzyl, β-phenetyl, 2-methoxyethyl, 4-phenylbutyl, 4-acetoxyethyl, 6-phenoxyhexyl, 12-phenyldodecyl, 18-phenyloctadecyl, heptadecylfluorooctyl, 12-(p-chlorophenyl)dodecyl, and 2-(diphenyl phosphate)ethyl), a straight-chain or branched unsubstituted alkenyl group having 2 to 40 carbon atoms (e.g., vinyl, allyl, 3-butenyl, 2-methyl-2-butenyl, 4-pentenyl, 3-pentenyl, 3-methyl-3-pentenyl, 5-hexenyl, 4-hexenyl, 3-hexenyl, 2-hexenyl, 7-octenyl, 9-decenyl, oleyl, linoleyl, and linolenyl), a straight-chain or branched substituted alkenyl group having 2 to 40 carbon atoms (e.g., 2-phenylvinyl, 4-acetyl-2-butenyl, 13-methoxy-9-octadecenyl, and 9,10-dibromo-12-octadecenyl), a straight-chain or branched unsubstituted alkynyl group having 2 to 40 carbon atoms (e.g., acetylene, propargyl, 3-butynyl, 4-pentynyl, 5-hexynyl, 4-hexynyl, 3-hexynyl, and 2-hexynyl), and a straight-chain or branched substituted alkynyl group having 2 to 40 carbon atoms (the substituent including, for example, an alkoxyl group and an aryl group) (e.g., 2-phenylacetylene and 3-phenylpropargyl).

The alicyclic compound group preferably includes, for example, a substituted or unsubstituted cycloalkyl group having 3 to 40 carbon atoms (e.g., cyclopropyl, cyclohexyl, 2,6-dimethylcyclohexyl, 4-tert-butylcyclohexyl, 4-phenylcyclohexyl, 3-methoxycyclohexyl, and cycloheptyl) and a substituted or unsubstituted cycloalkenyl group having 4 to 40 carbon atoms (e.g., 1-cyclohexenyl, 2-cyclohexenyl, 3-cyclohexenyl, 2,6-dimethyl-3-cyclohexenyl, 4-tert-butyl-2-cyclohexenyl, 2-cycloheptenyl, and 3-methyl-3-cycloheptenyl).

The aromatic group preferably includes, for example, a substituted or unsubstituted aryl group having 6 to 50 carbon atoms (the substituent including, for example, an alkyl group, an alkoxyl group, an aryl group, and a halogen atom) (e.g., phenyl, 1-naphtyl, 2-naphtyl, anthranyl, o-cresyl, m-cresyl, p-cresyl, p-ethylphenyl, p-tert-butylphenyl, 3,5-di-tert-butylphenyl, p-n-amylphenyl, p-tert-amylphenyl, 2,6-dimethyl-4-tert-butylphenyl, p-cyclohexylphenyl, octylphenyl, p-tert-octylphenyl, noylphenyl, p-n-dodecylphenyl, m-methoxyphenyl, p-butoxyphenyl, m-octyloxyphenyl, biphenyl, m-chlorophenyl, pentachlorophenyl, and 2-(5-methylnaphthyl)).

Preferred examples of the heterocyclic ring include a substituted or unsubstituted cyclic ether having 4 to 40 carbon atoms (e.g., furyl, 4-butyl-3-furyl, pyranyl, 5-octyl- 2H-pyran-3-yl, isobenzofuranyl, and chromenyl) and a substituted or unsubstituted nitrogen-containing ring having 4 to 40 carbon atoms (e.g., 2H-pyrrolyl, pyrrolyl, imidazolyl, pyrazolyl, indolizinyl, and morpholyl).

Out of them, a straight-chain, cyclic, or branched unsubstituted alkyl group having 1 to 24 carbon atoms (e.g., methyl, ethyl, n-propyl, n-butyl, n-amyl, n-hexyl, cyclohexyl, n-heptyl, n-octyl, 2-ethylhexyl, n-nonyl, 1,1,3-trimetylhexyl, n-decyl, n-dodecyl, cetyl, hexadecyl, 2-hexyldecyl, octadecyl, eicosyl, 2-octyldodecyl, docosyl, tetracosyl, and 2-decyltetradecyl), a straight-chain, cyclic, or branched substituted alkyl group having 1 to 24 carbon atoms with the carbon atoms in the substituent excluded (e.g., 6-phenoxyhexyl, 12-phenyldodecyl, 18-phenyloctadecyl, heptadecylfuluorooctyl, 12-(p-chlorophenyl)decyl, and 4-tert-butylcyclohexyl), a straight-chain, cyclic, or branched unsubstituted alkenyl group having 2 to 24 carbon atoms (e.g., vinyl, allyl, 2-methyl-2-butenyl, 4-pentenyl, 5-hexenyl, 3-hexenyl, 3-cyclohexenyl, 7-octenyl, 9-decenyl, oleyl, linoleyl, and linolenyl), a straight-chain, cyclic, or branched substituted alkenyl group having 2 to 24 carbon atoms (e.g., 2-phenylvinyl and 9,10-dibromo-12-octadecenyl), and a substituted or unsubstituted aryl group having 6 to 30 carbon atoms (e.g., phenyl, 1-naphthyl, 2-naphthyl, p-cresyl, p-ethylphenyl, p-tert-butylphenyl, p-tert-amylphenyl, octylphenyl, p-tert-octylphenyl, nonylphenyl, p-n-dodecylphenyl, m-octyloxyphenyl, and biphenyl) are particularly preferable.

$Q_1$, $Q_2$, and $Q_3$ in formula (I) each independently represent one selected from the group consisting of a single bond, an oxygen atom, a sulfur atom, or —N($R_3$)— in which $R_3$ represents a hydrogen atom or a group represented by $R_2$ that is defined above. Out of them, a single bond, an oxygen atom and —N($R_3$)— are preferable and particularly preferably at least two of $Q_1$, $Q_2$, and $Q_3$ are oxygen atoms. Herein, by "a single bond" is meant that no elements are present. $Q_4$, $Q_5$, and $Q_6$ in formula (II) have the same meanings as defined above for $Q_1$, $Q_2$, and $Q_3$ in formula (I), except that all of $Q_4$, $Q_5$, and $Q_6$ are not oxygen atoms at the same time.

L in formulas (I) and (II) represents a divalent linking group and preferably denotes a group represented by the following formula (III):

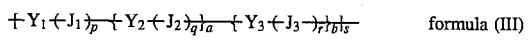  formula (III)

In the formula, $Y_1$, $Y_2$, and $Y_3$, which are the same or different, each represent a substituted or unsubstituted alkylene group having 1 to 40 carbon atoms or a substituted or unsubstituted arylene group having 6 to 40 carbon atoms (the substituent is the same as those defined in $R_1$); and preferably the alkylene group includes, for example, a methylene group, an ethylene group, a propylene group, a trimethylene group, a tetramethylene group, a pentamethylene group, a hexamethylene group, a 1,4-cyclohexylene group, an octamethylene group, a decamethylene group, and a 2-methoxy-1,3-propylene group; and the arylene group includes, for example, an o-phenylene group, an m-phenylene group, a p-phenylene group, a 3-chloro-1,4-phenylene group, a 1,4-naphthylene group, and a 1,5-naphthylene group. Out of these, an ethylene group, a propylene group, a trimethylene group, a tetramethylene group, a pentamethylene group, a hexamethylene group, a 1,4-cyclohexylene group, an octamethylene group, a decamethylene group, an m-phenylene group, and a p-phenylene group are particularly preferable.

$J_1$, $J_2$, and $J_3$, which are the same or different, each represent a divalent linking unit, which includes preferably a single bond, —O—, —S—, —CO—, —COO—, —OCO—, —CON($R_4$)— in which $R_4$ represents a hydrogen atom, an unsubstituted alkyl group having 1 to 6 carbon atoms, or a substituted alkyl group having 1 to 6 carbon atoms with the carbon atoms in the substituent excluded (the substituent including, for example, an aryl group, an alkoxyl group, and a halogen atom), —N($R_4$)CO— in which $R_4$ has the same meaning as defined above, —CON($R_4$)CO— in which $R_4$ has the same meaning as defined above, —N($R_4$)CON($R_5$)— in which $R_4$ and $R_5$, which are the same or different, have the same meaning as that of $R_4$ defined above, —OCON($R_4$)— in which $R_4$ has the same meaning as defined above, —N($R_4$)COO— in which $R_4$ has the same meaning as defined above, —SO$_2$—, —SO$_2$N($R_4$)— in which $R_4$ has the same meaning as defined above, —N($R_4$)SO$_2$— in which $R_4$ has the same meaning as defined above, —N(COR$_4$)— in which $R_4$ has the same meaning as defined above, and —OP(=O)(OR$_1$)O— in which $R_1$ has the same meaning as defined above. Out of these, for example, a single bond, —O—, —S—, —CO—, —COO—, —OCO—, —CON($R_4$)— in which $R_4$ represents a hydrogen atom, a methyl group, an ethyl group, or a propyl group, —N($R_4$)CO— in which $R_4$ has the same meaning as defined above, —SO$_2$N($R_4$)— in which $R_4$ has the same meaning as defined above, and —N($R_4$)SO$_2$— in which $R_4$ has the same meaning as defined above are particularly preferable.

p, q, and r are each independently an integer of 0 to 5. Preferably p, q, and r are each independently an integer of 0 to 3 with particular preference given to an integer of 0 or 1. s is an integer of 1 to 10, preferably 1 to 5, and particularly preferably 1 to 3.

a and b are each independently an integer of 0 to 50. Preferably a and b are each independently an integer of 0 to 20 with particular preference given to an integer of 0 to 10.

Z in formulas (I) and (II) represents an ionic group, preferably a hydrophilic anionic or cationic group, and particularly preferably an anionic group in view of the photographic properties. The anionic group includes preferably —COOM, —SO$_3$M, —OSO$_3$M, and —PO(OM)$_2$—OPO(OM)$_2$ in which M represents a counter cation, preferably an alkali metal ion (e.g., a lithium ion, a sodium ion, and a potassium ion), an alkali earth metal ion (e.g., a magnesium ion and a calcium ion), or an ammonium ion, with particular preference given to a sodium ion and a potassium ion. The cationic ion includes preferably —NH$_3^+$.X$^-$, —NH$_2$(R$_6$)$^+$.X$^-$, —NH(R$_6$)$_2^+$.X$^-$, and —N(R$_6$)$_3^+$.X$^-$ in which $R_6$ represents an alkyl group having 1 to 3 carbon atoms (e.g., methyl, ethyl, 2-hydroxyethyl, n-propyl, and iso-propyl), with preference given to a methyl group and a 2-hydroxyethyl group. X represents a counter anion, preferably a halogen ion (e.g., a fluorine ion, a chlorine ion, and a bromine ion), an inorganic anion cluster (e.g., a hydroxide ion, a sulfate ion, a nitrate ion, and a phosphate ion), or an organic compound anion (e.g., an oxalate ion, a formate ion, an acetate ion, a propionate ion, a methanesulfonate ion, and a p-toluenesulfonate ion), with particular preference given to a chloride ion, a sulfate ion, a nitrate ion, and an acetate ion.

$R_2$ in formulas (I) and (II) represents a monovalent group selected from the group consisting of the groups defined above for $R_1$ or the groups defined above for —L—Z and if $R_2$ represents a monovalent group selected from the group consisting of the groups defined for $R_1$, the structure of the monovalent group is the same as that of $R_1$ present in the same molecule or is different from that of $R_1$ present in the same molecule. Further, if $R_2$ represents a monovalent group selected from the group consisting of the groups defined for —L—Z, the structure of the monovalent group is the same as that of —L—Z present in the same molecule or is different from that of —L—Z present in the same molecule. Preferably $R_2$ represents a group selected from the group consisting of the groups defined for $R_1$.

Further, preferably the total number of the carbon atoms of $R_1$ and $R_2$ is 6 or more but 80 or less, particularly preferably 8 or more but 50 or less.

Specific examples of preferable surface-active compounds for use in the present invention are given below, but the present invention is not restricted to them.

In the following formulas, "(2EH)$C_8H_{17}$" means 2-ethylhexyl group.

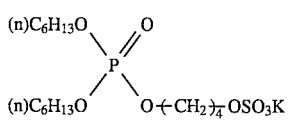

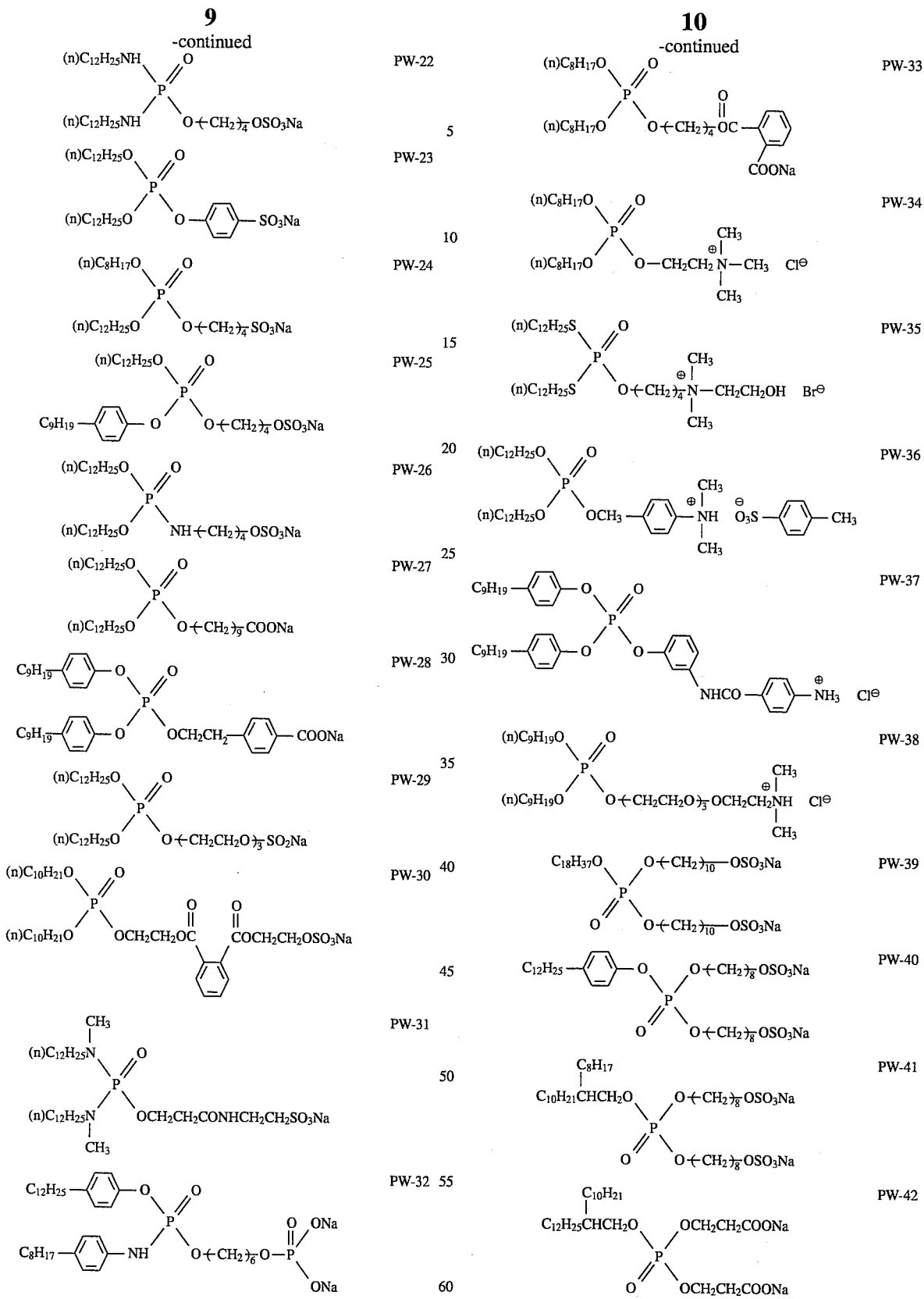

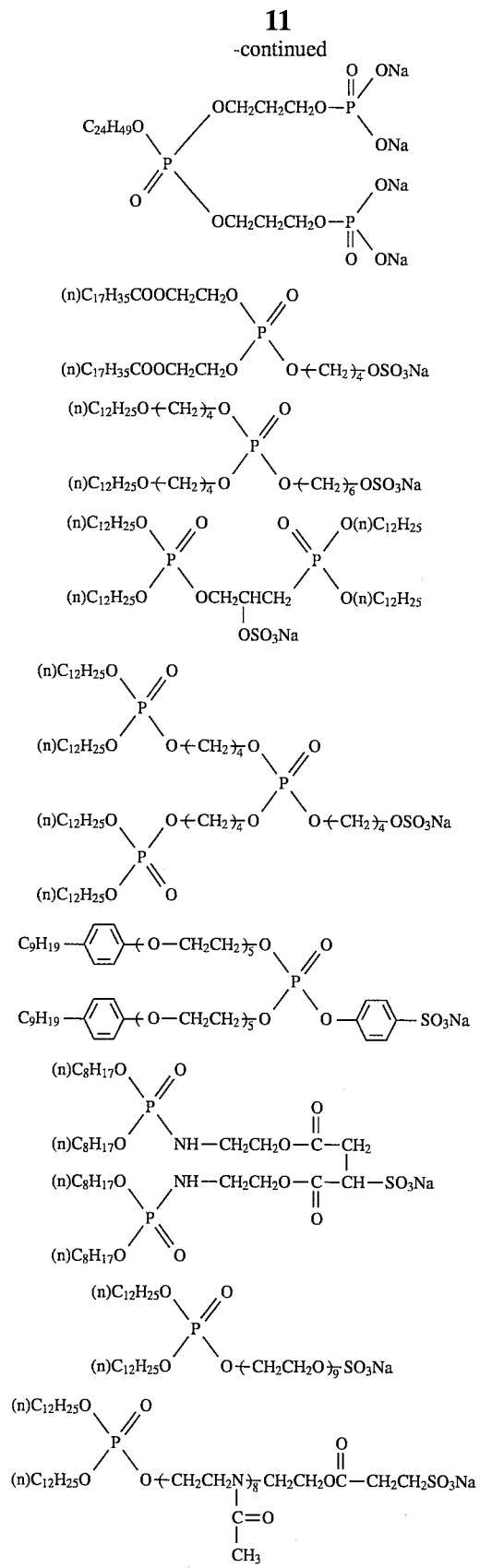

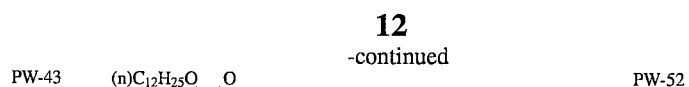

Each surface-active compound represented by formulas (I) and (II) of the present invention can be synthesized by the usual synthetic method. Typical examples of the synthetic method are shown below, but the present invention is not restricted to these specific synthetic examples.

SYNTHETIC EXAMPLE 1

Synthesis of Compound PW-4

1) Synthesis of di-2-ethylhexylphosphoryl chloride 26.0 Grams (0.2 mol) of 2-ethylhexyl alcohol was placed in a 200-ml three-necked flask equipped with a condenser and a stirrer, and it was cooled with ice to 5° C., with stirring. Then, 15.3 g (0.1 mol) of phosphorus oxychloride was added dropwise to the flask over 30 min with the internal temperature kept below 10° C., and after the completion of the addition the stirring was continued for 20 min. The temperature of the reaction mixture was then elevated to 25° C.; the reaction was continued for 1 hour under a pressure of 80 to 120 mmHg; and after the temperature was elevated to 50° C., the reaction was continued for 4 hours under the same reduced pressure. The reaction mixture was cooled to room temperature, to obtain 33.7 g of a transparent liquid (yield: 98.8%).

2) Synthesis of 4-hydroxybutyl-di-2-ethylhexyl phosphate 18.8 Grams (0.2 mol) of 1,4-butanediol and 15.2 g (0.15 mol) of triethylamine were placed in a 200-ml three-necked flask with a condenser and a stirrer, and then 33.7 g (0.099 mol) of the di-2-ethylhexylphosphoryl chloride synthesized above was added, dropwise over 30 min with stirring, under water cooling with the internal temperature kept below 30° C.; and after the completion of the addition the stirring was continued for 1 hour. The temperature of this reaction mixture was elevated to 50° C., and the reaction was allowed to proceed for 3 hours. The reaction mixture was cooled to room temperature; then 200 ml of ethyl acetate was added; the deposit was filtered; and the filtrate was condensed under reduced pressure and was subjected to column chromatography (eluent: ethyl acetate/hexane=2/1) on silica gel as a carrier, to purify and separate 16.8 g (yield: 43.0%) of the intended compound.

3) Synthesis of Compound PW-4

15.8 Grams (40 mmol) of the 4-hydroxybutyl-di-2-ethylhexyl phosphate synthesized above and 10 ml of chloroform were placed in a 200-ml three-necked flask equipped with a condenser and a stirrer; then 9.3 g (80 mmol) of chlorosulfonic acid was added dropwise over 30 min, under ice cooling with stirring the internal temperature kept below 15° C.; and after the completion of the addition, the stirring was continued for 2 hours at room temperature. 20 Milliliters of water was added slowly to this reaction mixture; then 50 ml of ethanol was added, to obtain a solution, and the pH was adjusted to 7.1 with 1N sodium hydroxide solution. 300 Milliliter of toluene was added to this reaction mixture; then, after azeotropic dehydration was repeated 5 times, the solution was condensed; then 300 ml of ethyl acetate was added, to dissolve it, and the solution was dehydrated with 80 g of anhydrous sodium sulfate, by allowing it to stand overnight. The solution was filtered to separate insoluble matter, and the filtrate was condensed under reduced pressure, to obtain 19.3 g (yield: 97.1%) of the intended Compound PW-4 of the present invention, in the form of a wax. The compound was identified by IR spectrum, $^1$H-NMR spectrum, and elemental analysis.

$^1$H-NMR (CDCL$_3$, δ): 0.8–1.1 (hydrocarbon chain CH$_3$, 12H), 1.2–1.5 (hydrocarbon chain CH$_2$, 16 H), 1.5–1.7 (hydrocarbon chain CH, 2H), 1.7–1.9 (tetramethylene chain CH$_2$, 4 H), 3.8–4.0 (hydrocarbon chain —CH$_2$O—, 4 H), 4.0–4.4 (tetramethylene chain —CH$_2$O—, 4 H)

IR 1320 cm$^{-1}$ (phosphate) 1230 cm$^{-1}$ (sulfate)

SYNTHESIS EXAMPLE 2

Synthesis of Compound PW-22

1) Synthesis of di-dodecylphosphoryl chloride 223.6 Grams (1.2 mol) of dodecyl alcohol and 500 ml of methylene chloride were placed in 1-liter three-necked flask equipped with a condenser and a stirrer; then 55.8 g (0.6 mol) of phosphorus oxychloride was added dropwise over 30 min, with stirring, under cooling with ice with the internal temperature kept below 10° C.; and after the completion of the addition the stirring was continued for 20 min. The temperature of this reaction mixture was elevated to room temperature, then the reaction was continued for 1 hour under reduced pressure of 80 to 120 mmHg; and after the temperature was elevated to 50° C., the reaction was continued for 3 hours under ordinary pressures. The reaction mixture was cooled to room temperature, to obtain 246.6 g (yield: 87.6%) of a transparent liquid.

2) Synthesis of Compound PW-22

87.1 Grams (0.5 mol) of previously dehydrated p-phenolsulfonic acid and 50.1 g (0.5 mol) of triethylamine were placed in a 1-liter three-necked flask equipped with a condenser and a stirrer; then 216.81 g (0.5 mol) of the didodecylphosphoryl chloride synthesized above was added dropwise over 30 min, under cooling with ice with stirring with the internal temperature kept below 30° C.; and after the completion of the addition the stirring was continued for 1 hour. The temperature of this reaction mixture was elevated to 50° C. and the reaction was allowed to proceed for 3 hours. The reaction mixture was cooled to room temperature; 200 ml of ethyl acetate was added; the deposit was filtered; the filtrate was condensed under reduced pressure and was subjected to column chromatography (eluent: ethyl acetate/hexane=4/1) on silica gel as a carrier, to separate a purified material. The obtained material was dissolved in 150 ml of methanol, and 21.0 g (0.55 mol) of sodium hydroxide was added to the solution, followed by stirring at room temperature for 8 hours. 500 Milliliter of toluene was added to the reaction mixture, and, after azeotropic dehydration was repeated five times, the solution was condensed; 800 ml of ethyl acetate was added, to dissolve the concentrate, and the solution was dehydrated with 80 g of anhydrous sodium sulfate, by allowing it stand overnight. The solution was filtered, to separate insoluble matter, and the filtrate was condensed under reduced pressure, to obtain 125.6 g (yield: 41.1%) of the intended Compound PW-22 of the present invention, in the form of a wax. The compound was identified by IR spectrum, $^1$H-NMR spectrum, and elemental analysis.

$^1$H-NMR (CDCL$_3$, δ): 0.8–1.1 (hydrocarbon chain CH$_3$, 6 H), 1.2–1.5 (hydrocarbon chain CH$_2$, 20 H), 3.8–4.0 (hydrocarbon chain —CH$_2$O—, 4 H), 7.3–8.1 (aromatic ring CH, 4 H)

IR 1320 cm$^{-1}$ (phosphate) 1230 cm$^{-1}$ (sulfate)

When the compound of the present invention is incorporated in a photographic material, the compound is used as a dispersant for hydrophobic photographically useful substances, or it is used as a coating aid, an antistatic agent, a slip agent, or a wetting improver; and the compound of the present invention has particularly excellent performance as a dispersant for hydrophobic photographically useful substances. When the compound of the present invention is incorporated in a processing solution for photography, the compound can be used as a dispersant for hydrophobic photographically useful substances, or as a wetting improver or an antistatic agent. Herein, "a processing solution for photography" includes various processing solutions for photography for conventional use, for example, a color developer, a bleaching solution, a fixing solution, a bleach-fixing solution, and a stabilizing solution. In the processing solution for photography of the present invention, the amount of the compound represented by the above formula (I) to be used is not particularly restricted, but the amount is usually in a range of 1 mg to 100 g, preferably 10 mg to 10 g, and more preferably 0.1 g to 5 g, per liter of processing solution.

The term "hydrophobic photographically useful compounds" that can be used in the present invention means any organic and inorganic compounds that are useful photographically. In the present invention, it is preferable to use an oil-soluble organic substance for photography. Herein the term "oil-soluble substances" means substances that are soluble in an amount of 3% by weight or more in organic solvents at room temperature (20° C.). By the term "organic solvents" is meant organic solvents described, for example, in "Solvent Handbook", and examples thereof include methanol, ethanol, isopropanol, butanol, ethyl acetate, isopropyl acetate, butyl acetate, acetone, methyl ethyl ketone, tetrahydrofuran, cyclohexanone, benzene, toluene, dioxane, acetonitrile, dichloromethane, and chloroform.

As hydrophobic photographically useful compounds that can be dispersed in the present invention, there can be mentioned, for example, a dye image-forming coupler, a dye image-donating redox compound, a stain-preventing agent, an antifoggant, an ultraviolet-absorbing agent, a discoloration-preventing agent, a color-mix-preventing agent, a nucleator, a dye image stabilizer, a solvent for silver halide, a bleaching accelerator, a dye for filter and its precursor, a dye, a pigment, a sensitizer, a film-hardening agent, a brightening agent, a desensitizer, a developing agent, an antistatic agent, an antioxidant, a developing agent scavenger, a mordant, and a dispersion oil and a dispersion polymer as a medium to disperse the above compound. As examples of description of these compounds, can be mentioned, for example, *Research Disclosure* Nos. 17643, 18716, and 307105.

a) Dye image-forming coupler

Compounds that forms colored or noncolored dye by coupling with the oxidized product of an aromatic primary amine developing agent is called a coupler. As couplers, a yellow coupler, a magenta coupler, a cyan coupler, and a black coupler are useful.

As yellow couplers that can be used in the present invention, an oil protected type acylacetamide series coupler can be mentioned as a representative example. The concrete examples are described, for example, in U.S. Pat. Nos. 2,407,210, 2,875,057, and 3,265,506. As 2-equivalent yellow couplers, can be mentioned oxygen atom-releasing type yellow couplers described, for example, in U.S. Pat. Nos. 3,408,194, 3,447,928, 3,933,501, and 4,022,620, or nitrogen atom-releasing type yellow couplers described, for example, in JP-B ("JP-B" means examined Japanese patent publication) No. 10739/1983, U.S. Pat. Nos. 4,401,752 and 4,326,024, *Research Disclosure* No. 18053 (April 1979), U.S. Pat. No. 1,425,020, and West German Patent Application (OLS) Nos. 2,219,917, 2,261,361, 2,329,587, and 2,433,812, as representative examples. α-Pivaloylacetoanilide series couplers are excellent in fastness of colored dye, especially in light fastness, while α-benzoylacetoanilide series couplers can give a high color density.

Among them, those described, for example, in U.S. Pat. Nos. 3,933,501, 4,022,620, 4,326,024, 4,401,752, and 4,248,961, JP-B No. 10739/1983, British Patent Nos. 1,425,020 and 1,476,760, U.S. Pat. Nos. 3,973,968, 4,314,023, and 4,511,649, and European Patent No. 249,473A are preferable.

As magenta couplers that can be used in the present invention, an oil protected type indazolone series coupler or a cyanoacetol series coupler (preferably 5-pyrazolone series and pyrazoazole series such as pyrazolotriazoles) can be mentioned. As 5-pyrazolone series couplers, couplers 3-position of which is substituted with an arylamino group or an acylamino group are preferable, in view of the hue and color density of colored dye, and representative examples are described, for example, in U.S. Pat. Nos. 2,311,082, 2,343,703, 2,600,788, 2,908,573, 3,062,653, 3,152,896, and 3,936,015. As coupling-off groups of 2-equivalent 5-pyrazolone series coupler, a nitrogen atom coupling-off group described in U.S. Pat. No. 4,310,619 and an arylthio group described in U.S. Pat. No. 4,351,897 are preferable. In the case of 5-pyrazolone series coupler having a ballast group described in, for example, European Patent No. 73,636, a high color density can be obtained.

As pyrazoloazole series coupler can be mentioned pyrazolobenzimidazoles described, for example in U.S. Pat. No. 3,369,879, pyrazolo[5,1-c][1,2,4]triazoles described, for example in U.S. Pat. No. 3,725,067, and pyrazolopyrazoles described, for example in *Research Disclosure* No. 24220 (June 1984). Imidazo[1,2-b]pyrazoles described in European Patent No. 119,741 and pyrazolo[1,5-b][1,2,4]triazole described in European Patent No. 119,860 are preferable in view of less auxiliary absorbency of yellow and light fastness of colored dye.

Among them, those described in U.S. Pat. Nos. 4,310,619 and 4,351,897, European Patent No. 73,636, U.S. Pat. Nos. 3,061,432 and 3,725,067, *Research Disclosure* No. 24220 (June 1984), JP-A No. 33552/1985, *Research Disclosure* No. 24230 (June 1984), JP-A Nos. 43659/1985, 72238/1986, 35730/1985, 118034/1980, and 185951/1985, U.S. Pat. Nos. 4,500,630, 4,540,654, and 4,556,630 and International Publication No. WO88/04795 are preferable.

As cyan couplers that can be used in the present invention, oil protected type naphthol series and phenol series couplers can be mentioned, and their representative examples include a naphthol coupler described in U.S. Pat. No. 2,474,293, preferably an oxygen atom-releasing type 2-equivalent naphthol series coupler described, for example in U.S. Pat. Nos. 4,052,212, 4,146,396, 4,228,233, and 4,296,200. The concrete examples of phenol series couplers are described, for example in U.S. Pat. Nos. 2,369,929, 2,801,171, 2,772,162, and 2,895,826. Cyan couplers that is fast to humidity and temperature are preferably used in the present invention, and their representative examples include a phenol series cyan coupler having an alkyl group higher in carbon atom numbers than ethyl group at the meta position of phenol nucleus, described in U.S. Pat. No. 3,772,002, 2,5-diacylamino-substituted phenol series coupler described, for example, in U.S. Pat. Nos. 2,772,162, 3,758,308, 4,126,396, 4,334,011, and 4,327,173, West German Patent Application (OLS) No. 3,329,729, and JP-A No. 166956/1984, and a phenol series coupler having a phenylureide group at 2-position and an acylamino group at 5-position described in, for example U.S. Pat. Nos. 3,446,622, 4,333,999, 4,451,559, and 4,427,767.

Naphthol series couplers which is substituted with a sulfonamide group, an amide group or the like at 5-position described, for example in JP-A Nos. 37448/1985, 153640/1986, and 14557/1986 are excellent in particularly fastness of colored dye, and are preferable ones. Further, pyrazoloazole series couplers described, for example in JP-A Nos. 553/1989, 554/1989, 555/1989, and 556/1989, and imidazole series couplers described in U.S. Pat. No. 4,818,672 can be used.

Among them, those described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Application (OLS) No. 3,329,729, European Patent Nos. 121,365A and 249,453A, U.S. Pat. Nos. 3,446,622, 4,333,999, 4,775,616, 4,451,559, 4,427,767, 4,690,889, 4,254,212, and 4,296,199, and JP-A No. 42658/1986 are particularly preferable.

Typical examples of polymerized dye-forming coupler are described in, for example, U.S. Pat. Nos. 3,451,820, 4,080,211, 4,367,282, 4,409,320, and 4,576,910, British Patent No. 2,102,137, and European Patent No. 341,188A.

As a coupler which forms a colored dye having moderate diffusibility, those described in U.S. Pat. No. 4,366,237, British Patent No. 2,125,570, European Patent No. 96,570, and West German Patent Application (OLS) No. 3,234,533 are preferable.

As a colored coupler to rectify the unnecessary absorption of colored dyes, those couplers described in, paragraph VII-G of *Research Disclosure* No. 17643, paragraph VII-G of ibid. No. 307105, U.S. Pat. No. 4,163,670, JP-B No. 39413/1982, U.S. Pat. Nos. 4,004,929 and 4,138,258, and British Patent No. 1,146,368 are preferable. Further, it is preferable to use couplers to rectify the unnecessary absorption of colored dyes by a fluorescent dye released upon the coupling reaction as described in U.S. Pat. No. 4,774,181 and couplers having a dye precursor, as a group capable of being released, that can react with the developing agent to form a dye as described in U.S. Pat. No. 4,777,120.

A compound that releases a photographically useful residue accompanied with the coupling reaction can be used favorably in this invention. As a DIR coupler that release a development inhibitor, those described in patents cited in paragraph VII-F of the above-mentioned *Research Disclosure* No. 17643 and in paragraph VII-F of ibid. No. 307105, JP-A Nos. 151944/1982, 154234/1982, 184248/1985, 37346/1988, and 37350/1988, and U.S. Pat. Nos. 4,248,962 and 4,782,012 are preferable. A coupler that release a bleaching accelerator, described in *Research Disclosure* Nos. 11449 and 24241 and JP-A No. 201247/1986, is effective for shortening the time of processing that has bleaching activity, and the effect is great in the case wherein the coupler is added in a photographic material using the above-mentioned tabular silver halide grains. As a coupler that releases, imagewise, a nucleating agent or a development accelerator upon developing, those described in British Patent Nos. 2,097,140 and 2,131,188, and JP-A Nos. 157638/1984 and 170840/1984 are preferable. Further, compounds which release a fogging agent, a developing accelerator, or a solvent for silver halide by a oxidation-reduction reaction with the oxidized product of developing agent as described in JP-A Nos. 107029/1985, 252340/1985, 44940/1989, and 45687/1989 are also preferable.

Other compounds that can be incorporated in the photographic material of the present invention include competitive couplers described in U.S. Pat. No. 4,130,427, multi-equivalent couplers described in U.S. Pat. Nos. 4,283,472, 4,338,393, and 4,310,618, couplers which release a DIR redox compound, couplers which release a DIR coupler, and redox compounds which release a DIR coupler or a DIR redox as described in JP-A Nos. 185950/1985 and 24252/1987, couplers which release a dye to regain a color after releasing as described in European Patent Nos. 173,302A and 313,308A, couplers which release a ligand as described in U.S. Pat. No. 4,555,477, couplers which release a leuco dye as described in JP-A No. 75747/1988, and couplers which release a fluorescent dye as described in U.S. Pat. No. 4,774,181.

Couplers above-described can be used in a combination of two or more thereof in the same layer in order to satisfy the desired properties for a photographic material.

b) Dye image-donating redox compounds

Other hydrophobic compounds that can be used in the present invention are dye image-donating redox compounds used in color-diffusion-transfer-process photographic materials. As is known to those skilled in the art, these compounds include negative-type compounds and positive-type compounds, and when they are processed with an alkaline processing composition, they are initially mobile or immobile in the photographic element.

Negative-type dye image-donating compounds useful for the present invention include couplers that form or release dyes when reacted with oxidized color-developing agents, and specific examples thereof are described, for example, in U.S. Pat. No. 3,227,550 and Canadian Patent No. 602,207.

Preferable negative-type dye image-donating compounds for use in the present invention include dye-releasing redox compounds, which release dyes when reacted with developing agents in the oxidized state, or with electron transfer agents, and typical specific examples thereof are described, for example, in JP-A Nos. 33826/1973, 113624/1976, 54021/1979, and 71072/1971. Immobile positive-type dye image-donating compounds that can be used in the present invention include compounds that release a diffusible dye without receiving electrons at all (i.e., without being reduced) during photographic processing under alkaline conditions, or after receiving at least one electron (i.e., after being reduced).

Further, positive dye image-donating compounds that are mobile from the onset under alkaline photographic processing conditions include dye-developing agents, which are effective in the present invention. Typical specific examples thereof are described, for example, in JP-B Nos. 32130/1973 and 22780/1980.

The dyes formed from the dye image-donating compounds for use in the present invention may be the same dyes as existing dyes, or they may be dye precursors that can be converted to dyes in a photographic processing step or in an additional processing stage, and the final image dye may or may not be metallized. Typical dye structures useful for the present invention are metallized or non-metallized dyes of azo dyes, azomethine dyes, anthraquinone dyes, and phthalocyanine dyes. Among these, azo series cyan, magenta, and yellow dyes are particularly important.

As one type of dye precursor, a dye-releasing redox compound having a dye part wherein the light absorption is temporarily shifted in the photosensitive element, can be used in the present invention.

Particularly preferable dye image-donating compounds for use in the present invention include dye-releasing redox compounds (DRR-compounds) and specific examples thereof are described, for example, in the above-mentioned JP-A Nos. 33826/1973, 113624/1976, 54021/1979, and 71072/1981. Specific examples of a redox mother nucleus that releases a diffusible dye under alkaline conditions when cross-oxidized by the development of a silver halide are, for example,

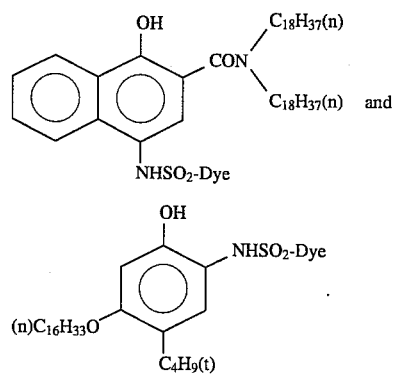

Particularly preferable dye-donating compounds of other type are of the positive-type and are described in JP-A Nos. 110827/1978, 110828/1978, and 164342/1981, and specific examples of the redox mother nucleus of this type include

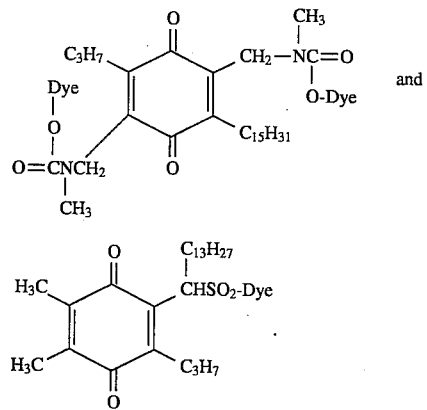

Specific examples of the dye-releasing redox compound include compounds described in JP-A No. 1/1986 ((DR-1) to (DR-14), described on pages 23 to 15).

c) Ultraviolet-absorbing agents

Ultraviolet-absorbing agents suitable for practice of the present invention are described, for example, in JP-B Nos. 21687/1967 and 5496/1973, JP-A No. 1026/1972, and British Patent No. 1,293,982. Out of them, the oil-soluble ultraviolet-absorbing agents are particularly preferable.

d) Organic or inorganic dyes and pigments

Dyes and pigments for use in the present invention include organic dyes and pigments or inorganic dyes and pigments, such as azo series, azomethine series, oxonol series, cyanine series, phthalocyanine series, quinacridone series, anthraquinone series, dioxazine series, indigo series, perynone/perylene series, titanium oxide, cadmium series, iron oxide series, chromium oxide, and carbon black, as well as known dyes that are conventionally used as colorants, or mixtures of these can also be used. These dyes and pigments in the present invention can be used in any form; for example, in the form of an aqueous paste or in the form of a powder, immediately after the production. In particular the present invention is useful in dispersing oil-soluble dyes described, for example, in U.S. Pat. No. 4,420,555 and JP-A Nos. 204630/1986 and 205934/1986.

Oil-soluble dyes particularly useful in the present invention are described below.

Particularly useful dyes for use in the present invention may be any of various known dyes. The structure of these dyes includes, for example, arylidene compounds, heterocyclic arylidene compounds, anthraquinones, triarylmethanes, azomethine dyes, azo dyes, cyanines, merocyanines, oxonols, styryl dyes, phthalocyanine, and indigo. Preferably the dyes used in the present invention are insoluble in water and the solubility in ethyl acetate is 10 g/liter or more (40° C.) and the structure of the chromophore is not important.

The arylidene compound is one wherein an acid nucleus and an aryl group are connected through one or more methine groups.

The acid nucleus includes, for example, 2-pyrazolin-5-one, 2-isooxazolin-5-one, barbituric acid, 2-thiobarbituric acid, benzoylacetonitrile, cyanoacetamide, cyanoacetanilide, a cyanoacetate, a malonate, malondianilide, dimedone, benzoylacetanilide, pivaloylacetanilide, malononitrile, 1,2-dihydro-6-hydroxypyridin-2-one, pyrazolidin-3,5-dione, pyrazolo[3,4-b]pyridin-3,6-dione, indan-1,3-dione, hydantoin, thiohydantoin, and 2,5-dihydro-furan-2-one.

The aryl group includes a phenyl group, which is preferably substituted by an electron-donating group, such as an alkoxyl group, a hydroxyl group, and an amino group.

The heterocyclic arylidene compound is one wherein an acid nucleus and a heteroaromatic ring are connected through one or more methine groups.

The acid nucleus includes those mentioned above.

The heteroaromatic ring includes, for example, pyrrole, indole, furan, thiophene, pyrazole, and cumarin.

The anthraquinones are those wherein the anthraquinone is substituted by an electron-donating group or an electron-attracting group.

The triarylmethanes are compounds wherein three substituted-aryl groups (which are the same or different) are bonded to one methine group. For example, phenolphthalein is mentioned.

The azomethine dyes are those wherein an acid nucleus and an aryl group are connected through an unsaturated nitrogen-linking group (azomethine group). The acid nucleus include, in addition to the acid nucleuses mentioned above, couplers known for photography can be mentioned. Indoanilines are also included in azomethine dyes.

Azo dyes are those wherein an aryl group or a heteroaromatic ring group is connected through an azo group.

Cyanines are those wherein two basic nucleuses are connected through one or more methine groups. The basic nucleus includes quaternary salts of, for example, oxazole, benzoxazole, thiazole, benzothiazole, benzimidazole, quinoline, pyridine, indolenine, benzoindolenine, benzoselenazole, and imidazoquinoxaline, and pyrylium.

Melocyanine dyes are those wherein the above basic nucleus and acid nucleus are connected through a double bond or one or more methine groups.

The oxonol dyes are those wherein two of the above acid nuclei bonded through one methine group or three or more odd methine groups.

The styryl dyes are those wherein the above basic nucleus and an aryl group are connected through two or four methine groups.

The phthalocyanine is one to which a metal is coordinated or is not coordinated.

The indigo is substituted or is not substituted and includes thioindigo.

e) Other hydrophobic compounds

Other hydrophobic compounds that can be used in the present invention are electron donors (hereinafter referred to as "ED") that can donate at least one electron to an oxidation type dye-donating compound or the oxidized product of a color-developing agent. Effective ED's are compounds having the partial structure of Kendal-Pliz as described by T. H. James in *The Theory of the Photographic Process*, fourth edition, Chapter 11. Compounds belonging to this group are, for example, hydroquinones, catechols, o-aminophenols, and p-aminophenols. Desirably the ED compounds used in the present invention are low in diffusibility when incorporated in a photographic material layer. Low-diffusible or nondiffusible hydroquinones, pyrogallols, etc. are widely used, for example, as color-mix inhibitors, antioxidants, and antidiscoloring agents. Specific compound examples of these are 2,5-di-n-octylhydroquinone, 2,5-di-t-pentadecylhydroquinone, n-dodecyl gallate, and p-laurylamidepyrogallol.

As ED precursors that can be used in the present invention, compounds that are suitably used in combination with positive-type dye image-donating compounds can be mentioned. Examples thereof includes saccharin series compounds as described in U.S. Pat. No. 4,263,393 and active methine compounds as described in U.S. Pat. No. 4,278,750.

Other hydrophobic compounds that can be used in the present invention are, for example, development inhibitors and antifoggants represented, for example, by mercaptotetrazoles, mercaptotriazoles, mercaptopyrimidines, mercaptobenzimidazoles, mercaptothiadiazoles, benzotriazoles, and imidazoles; developing agents, such as p-phenylenediamines, hydroquinones, and p-aminophenols; auxiliary developing agents represented by pyrazolidones; nucleators, such as hydrazines and hydrazides; silver halide solvents, such as hypo; bleach accelerators, such as aminoalkyl thiols; or dyes, such as azo dyes and azomethine dyes. Precursors of the above hydrophobic compounds and hydrophobic compounds which has such a redox function that the above hydrophobic compound is released along with the progress of the development, for example, dye materials for the above-mentioned color diffusion transfer process photographic materials as well as DIR- or DAR-hydroquinones can be mentioned as good hydrophobic compounds as well. The above hydrophobic compounds may be bonded through a timing group and such a timing group includes, for example, those described in JP-A No. 145135/1979 that can release a photographically useful substance when underwent an intramolecular ring closure reaction, those described, for example, in British Patent No. 2,072,363 and JP-A No. 154234/1982 that can release a photographically useful substance by intramolecular electron transfer reaction, those described, for example, in JP-A No. 179842/1982 that can release a photographically useful substance with carbon dioxide given off, and those described in JP-A No. 93442/1984 that can release a photographically useful substance with formalin given off.

f) Polymers for dispersion

As high-boiling organic substances (oil components for dispersion) that are used for suppressing crystallization of a hydrophobic compound that is dispersed finely in an aqueous medium, the below mentioned high-boiling organic substances are used and in addition polymer compounds can also be used as mediums for dispersion. As these polymer compounds, those virtually insoluble in water are preferable and can be chosen from hydrophobic organic polymers. Specific examples thereof are poly(methyl methacrylate), poly(ethyl methacrylate), poly(ethyl acrylate), poly(cyclohexyl methacrylate), poly(N-tert-butyl acrylamide), and poly(N-tert-octyl acrylamide).

In the present invention, to dissolve the hydrophobic compound, in addition to the above high-boiling organic substance, a low-boiling organic solvent (having a boiling point of 130° C. or below under one atmospheric pressure) immiscible with water or an organic solvent miscible with water can be used. To increase the stability of the obtained dispersion, the water-immiscible or water-miscible organic solvent used for making the photographically useful substance in the state of a solution may be removed by distillation, more preferably by distillation under reduced pressure, or by ultrafiltration or other known method.

As the organic solvents, for example, propylene carbonate, methyl acetate, ethyl acetate, isopropyl acetate, butyl acetate, ethyl propionate, sec-butyl alcohol, methyl ethyl ketone, 2-pentanone, 3-pentanone, cyclohexanone, dimethylformamide, and dimethyl sulfoxide can be mentioned. A preferable amount of the organic solvent to be used is 0.1 to 100 times the weight amount of the hydrophobic compound to be dispersed.

As a method of dispersing the hydrophobic photographically useful substance by using the compound of the present invention, typically the oil-in-water dispersion method, in which a high-boiling solvent is used in the presence of the surface-active agent of the present invention, can be mentioned.

Specifically, a dispersion can be prepared by mixing the hydrophobic compound, which is kept in the state of a solution by any of the below-mentioned methods, with water or an aqueous hydrophilic colloid solution in the presence of the compound of the present invention. If required, in order to make further fine the size of the particles of the dispersion, the below-mentioned dispersing machine may be used.

As the dispersing machine that is used for performing the present invention, for example, a high-speed stirring-type dispersing machine having a great shearing force, and a dispersing machine that can give high-intensity ultrasonic energy, can be mentioned. Specifically, a colloid mill, a homogenizer, a capillary-type emulsifier, a liquid siren, an electromagnetic stress-supersonic wave generator, and an emulsifier with a Poleman whistle, can be mentioned. A high-speed stirring-type dispersing machine that is preferably used for the present invention is a dispersing machine of the type in which the essential part having a dispersing function is rotated at a high speed (500 to 15,000 rpm, preferably 2,000 to 4,000 rpm) in a liquid, such as a dissolver, a Polytron, a homomixer, a Homoblender, a KD-mill, and a jet agiter. The high-speed stirring-type dispersing machine used for the present invention is also called a dissolver or a high-speed impeller dispersing machine, and a preferable example is described in JP-A No. 129136/1980, which machine comprises an impeller having a serrated blade bent alternately along a vertical shaft that is rotated at a high speed.

When a dispersion containing a hydrophobic compound is prepared in accordance with the present invention, various processes can be used. When a hydrophobic compound is dissolved in an organic solvent, the hydrophobic compound is dissolved in one solvent selected from the group consisting of the below-mentioned high-boiling organic substances, water-immiscible low-boiling organic solvents, or water-miscible organic solvents, or the hydrophobic compound is dissolved in an arbitrary mixture made up of two or more solvents selected from the above group, and then is dispersed in water or an aqueous hydrophilic colloid solution in the presence of a polymer represented by formula (I) of the present invention. In this case, the polymer of the present invention is allowed to be present in at least one of the solutions containing the hydrophobic compound, the water, and the aqueous hydrophilic colloid solution.

As the method of mixing the oil liquid containing the hydrophobic compound with the aqueous liquid, the so-called normal mixing method, in which the aqueous liquid is added to the oil liquid under stirring, or the reversed mixing method can be used; and out of them, the phase inversion method, which is of one type of reversed mixing method, is preferable, because a finer aqueous dispersion can be obtained.

In the present invention, although a hydrophobic compound can be dispersed stably in either water or a hydrophilic colloid composition, it is preferably dispersed in a hydrophilic colloid composition.

As the hydrophilic colloid in the hydrophilic colloid composition used in the present invention, a binding material or a protective colloid generally used for silver halide photographic materials is used.

As the binding material and the protective colloid for photographic emulsions, gelatin is advantageously used and other hydrophilic colloids can also be used. For example, the following can be used: proteins, such as gelatin derivatives, graft polymers of gelatin with other polymers, albumin, and casein; saccharide derivatives, such as cellulose derivatives including hydroxyethyl cellulose, carboxymethylcellulose, and cellulose sulfate, sodium alginate, and starch derivatives; and various synthetic hydrophilic polymers including homopolymers and copolymers, such as polyvinyl alcohols, polyvinyl alcohol partial acetals, poly-N-vinyl pyrrolidones, polyacrylic acids, polymethacrylic acids, polyacrylamides, polyvinylimidazoles, and polyvinylpyrazoles.

As the gelatin, in addition to lime-processed gelatin, acid-processed gelatin as well as gelatin hydrolyzate and gelatin enzymolyte can be used. As the gelatin derivative, those obtained by reacting gelatin with various compounds, such as acid halides, acid anhydrides, isocyanates, bromoacetic acid, alkanesultones, vinylsulofonamides, maleinimide compounds, polyalkylene oxides, and epoxy compounds can be used.

When an oil-soluble dye is used as a filter dye or an antihalation dye, an arbitrary effective amount can be used and preferably it is used in such an amount that the optical density will be in the range of 0.05 to 3.5. The timing when it is added may be at any stage before the coating is carried out.

The specific amount of the dye varies depending, for example, on the type of the dye, the polymer for dispersion, and the dispersion method and it is found that a preferable amount is generally in the range of $10^{-3}$ to 3.0 g/m$^2$, particularly $10^{-3}$ to 1.0 g/m$^2$.

Examples of high-boiling solvents used in the oil-in-water dispersion method are described, for example, in U.S. Pat. No. 2,322,027 and International Publication Patent No. WO 91/17480 and specific examples of high-boiling organic solvents having a boiling point of 175° C. or over under normal pressures are phthalates (e.g., dibutyl phthalate, dicyclohexyl phthalate, di-2-ethylhexyl phthalate, decyl phthalate, bis(2,4-di-t-amylphenyl) phthalate, bis(2,4-di-t- amylphenyl) isophthalate, and bis(1,1-diethylpropyl) phthalate), phosphates or phosphonates (e.g., triphenyl phosphate, tricreysyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, and di-2-ethylhexylphenyl phosphonate), benzoates (e.g., 2-ethylhexyl benzoate, dodecyl benzoate, and 2-ethylhexyl-p-hydroxybenzoate), amides (e.g., N,N-diethyldecaneamide, N,N-diethyllaurylamide, and N-tetradecylpyrrolidone), alcohols and phenols (e.g., isostearyl alcohol and 2,4-di-tert-amylphenol), aliphatic carboxylates (e.g., bis(2-ethylhexyl) sebacate, dioctyl azelate, glycerol tributylate, isostearyl lactate, and trioctyl citrate), aniline derivatives (e.g., N,N-dibutyl-2-butoxy-5-tert-octylaniline), and hydrocarbons (e.g., paraffin, docecylbenzene, and diisopropylnaphthalene).

As described in World Patent Publication No. WO 93/3420, a method wherein the amount of a surface-active agent is increased to obtain a fine dispersion and then the excess surface-active agent is removed by washing with water, is effective.

The co-solvents or the surface-active agents can be removed by known methods, which are described, for example, in U.S. Pat. Nos. 2,322,027, 2,801,171, 2,946,360, 3,396,027, and 4,233,397.

Further, it is possible that, after the hydrophobic photographically useful substance is dissolved in an acid, an alkali, a water-miscible organic solvent, or a mixture of these, it may be deposited and dispersed by neutralizing the resulting mixture in the presence of the surface-active agent of the present invention, or by mixing the resulting mixture with water. It is also possible that the surface-active agent of the present invention may be added to the solution, which in turn is added directly to a coating liquid, to carry out the dispersion.

Typical examples of the dispersion method using this technique are described, for example, in British Patent No. 1,193,349 and U.S. Pat. Nos. 4,957,857 and 4,933,270, wherein the method is applied to photographic couplers, and examples are also described in JP-A No. 163453/1992, wherein the method is applied to other hydrophobic photographically useful substances.

If the hydrophobic photographically useful substance is a solid, it can be directly made into a fine particle solid dispersion by dispersing it in a medium in the presence of water and the surface-active agent of the present invention.

As a typical example, a solid dispersion of a dye can be mentioned, as described in WO 88/04794. It is also effective to apply it to other pigments, such as carbon black and titanium oxide.

To disperse it in a medium, it is generally dispersed mechanically; for example, by a ball mill, a sand grinder mill, or a colloid mill.

The surface-active agent of the present invention can be used as an emulsifier when an aqueous polymer latex is synthesized by emulsion polymerization, and the produced polymer latex can be incorporated directly into a photographic material, or it is possible that, after a hydrophobic photographically useful substance is loaded into the produced polymer latex, the polymer latex may be incorporated into a photographic material.

The dispersion method by using a polymer latex is described, for example, in U.S. Pat. No. 4,199,363 and West German Patent Application (OLS) Nos. 2,541,274 and 2,541,230.

In the above-mentioned dispersion methods, the compound of the present invention may be used at the time of dispersion as described above; or, if necessary, after some other surface-active agent is used at the time of dispersion, the compound of the present invention can be added after the dispersion, for example, to improve stability; or the compound of the present invention can be used in combination with some other surface-active agent.

If the compound of the present invention is incorporated into at least one layer of the photographic material, the layer into which the compound of the present invention is incorporated is not particularly restricted, and examples of that layer are a surface-protective layer, an emulsion layer, an intermediate layer, an undercoat layer, a back layer, and other auxiliary layers.

The amount of the compound of the present invention to be used depends on the type and thickness of the photographic material; on the number of the layers to which the compound is added; on the type and amount of the substance that is to be dispersed; and on whether or not some other surface active agent is also added, and the amount is 0.0001 to 1 $g/m^2$ more preferably 0 0005 to 0 5 $g/m^2$ as the total amount in a photographic material.

The photographic material of the present invention will be described below.

Preferably the photographic material of the present invention includes a white-and-black photographic material, a radiographic material, a graphic photographic material, a color photographic material, and a color paper, which material may be a positive photographic material or a negative photographic material, and may be in the form of a roll or a sheet. In particular, a color photographic material is preferable, and typical examples thereof are a color reversal film and a color negative film.

Use of the compound of the present invention has made it possible to stably obtain quite-fine dispersed particles of a photographically useful compound, even when the compound is used in a small amount. Further, the obtained dispersed particles are excellent in production adaptability; excellent in that a photographically useful compound can be introduced selectively into a specific layer without adversely influencing the reactivity of the photographically useful compound in the film and without adversely influencing the film quality; and excellent in reactivity in processing steps.

The present invention will now be described with reference to the following Examples in detail, but the present invention is not restricted to them.

EXAMPLE 1

Dispersion of a Coupler

The following formulation that included the below-mentioned yellow color-forming coupler was emulsified by stirring, to obtain Dispersions 1-1 to 1-10.

| Liquid I: | Gelatin solution (10%) | 67 g |
|---|---|---|
| Liquid II: | Below-mentioned coupler C-1 | 8 g |
| | Ethyl acetate | 15 ml |
| | Surface-active agent | 0.35 g |

Liquid I and Liquid II were dissolved and mixed at 60° C. and were emulsified by a homoblender at 15,000 rpm for 2 min, which emulsification was repeated three times, to obtain an emulsion.

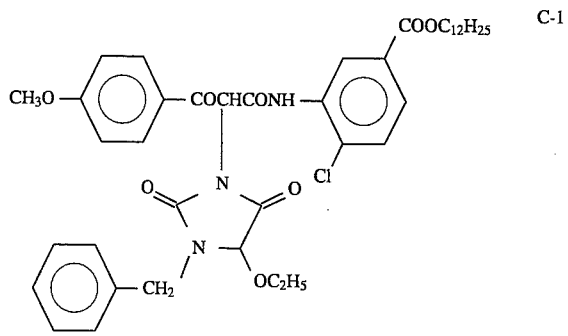

The surface-active agents, i.e., comparative compounds and compounds of the present invention, given in Table 1 were used for dispersion, and the particle size of each of the obtained dispersions was determined by the light-scattering method, using a Master Sizer manufactured by Malvern, and the results are given in Table 1.

TABLE 1

| Dispersion No. | Surface-active agent | Grain size (μm) | Height of foam (mm) | Solution stability after lapse of time | Remarks |
|---|---|---|---|---|---|
| 1-1 | Sodium dodecyl-benzene-sulphonate | 0.24 | 35 | xx | Comparative example |
| 1-2 | PW-3 | 0.17 | 10 | ○ | This invention |
| 1-3 | PW-4 | 0.17 | 10 | ○ | This invention |
| 1-4 | PW-6 | 0.18 | 5 | ⊙ | This invention |
| 1-5 | PW-11 | 0.17 | 10 | ⊙ | This invention |
| 1-6 | PW-12 | 0.21 | 5 | ⊙ | This invention |
| 1-7 | PW-14 | 0.21 | 10 | ⊙ | This invention |
| 1-8 | PW-9 | 0.22 | 15 | ⊙ | This invention |
| 1-9 | PW-31 | 0.21 | 10 | ○ | This invention |
| 1-10 | Sodium didodecyl-phosphate | 0.43 | 5 | x | Comparative example |

From the results given in Table 1, it can be understood that the compounds of the present invention, even when used in the same emulsifying amounts as those of other compounds, can make the particle size finer. In particular it can be understood that, in comparison with conventional 2-chain phosphate-type surface-active agents, namely sodium dodecylphosphate, which fall in the range of the Comparative examples, the compounds of the present invention are remarkably improved in emulsifying ability.

EXAMPLE 2

Foaming Test

One g of each of emulsions 1–1 to 1–10 prepared in Example 1 was placed in a test tube; 9 ml of water was added thereto; each mixture was heated, to bring about dissolution and was shaken at 25° C.; and then after 1 min, the foam was observed.

Evaluation was made on the height of the foam. The smaller the value is, the lower the foaming property is. The results are shown in Table 1.

It was shown that in comparison with the Comparative example, sodium dodecylbenzenesulfonate, which is excellent in emulsifying ability, any of the compounds of the present invention is low in foaming property, and the possibility of foaming in processing solutions is characteristically low.

EXAMPLE 3

Stability After the Lapse of Time

After the emulsions prepared in Example 1 were refrigerated at 5° C. for 3 weeks, they were dissolved by heating to 40° C. and were diluted with water in a 100 ml beaker, to make the volume tenfold greater, and the presence or absence of insoluble matter was observed.

Visual evaluation was classified into five ratings: xx, x, Δ, ○, and ⊙; the rating xx indicating that the insoluble matter was largest, and the rating ⊙ indicating that the insoluble matter was nil.

The results are also shown in Table 1.

It is shown that in comparison with the Comparative example, sodium dodecylbenzenesulfonate, which is high in emulsifying ability, many of the compounds of the present invention are easily dissolved and they are excellent in stability after the lapse of time under refrigeration.

EXAMPLE 4

A. Preparation of Emulsions

Emulsions shown in Table 2 were prepared in the same manner as in Example 1, except that the coupler was changed to the below-mentioned C-2. The particle diameter of the emulsions was determined by the turbidity method. That is, the emulsion was dissolved by heating at 40° C. and was diluted with water in a beaker, to make the volume twentyfold greater, and the particle diameter was relatively expressed by the ratio of the absorbance at 500 nm, measured by a spectrophotometer using 1 cm×1 cm optical cell, to the absorbance at 600 nm. The bigger the value of ratio between absorbances at 500 nm and at 600 nm is, which ratio is indicated with turbidity ratio in Table 2, the smaller the particle diameter of emulsion is.

B. Preparation and Evaluation of Photographic Materials

Layers having the below-mentioned compositions were applied on a triacetyl cellulose film support having an undercoat layer, thereby preparing Photographic Materials 401 to 406.

(1) Emulsion layer
  Tabular grain emulsion                           silver  1.70 g/m²
  (silver iodide: 10 mol %, average aspect
  ratio: 7.5, average grain diameter: 0.65 μm)
  Coupler C-2 (as a dispersion)                            0.77 g/m²
  C-2

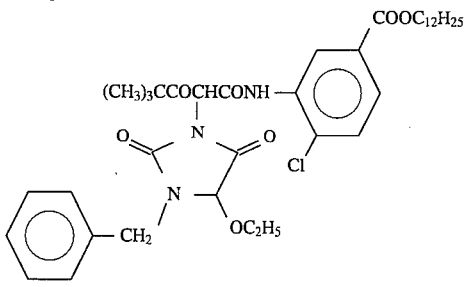

Gelatin                                                  3.50 g/m²
(2) Protective layer
  Sodium 2,4-dichloro-6-hydroxy-s-triazine                 0.15 g/m²
  Gelatin                                                  1.8  g/m²

These samples were given an white light for sensitometry, and were subjected to the development processing shown below. The yellow density of processed each sample was determined, to obtain a maximum density, and the result was shown in Table 2.

Herein, the development processing was conducted according to conditions shown below at 38° C.

| 1. Color development | 3 min 15 sec |
| 2. Bleaching         | 6 min 30 sec |
| 3. Washing           | 3 min 15 sec |
| 4. Fixing            | 6 min 30 sec |
| 5. Washing           | 3 min 15 sec |
| 6. Stabilizing       | 3 min 15 sec |

Compositions of processing solutions used are as follows:

| Color developer | |
| --- | --- |
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N-Ethyl-N-βhydroxyethylamino)-2-methylaniline sulfate | 4.5 g |
| Water to make | 1 liter |
| Bleaching solution | |
| Ammonium bromide | 160.0 g |
| Aqueous ammonia (28%) | 25.0 ml |
| Sodium iron ethylenediaminetertaacetate | 130 g |
| Glacial acetic acid | 14 ml |
| Water to make | 1 liter |
| Fixing solution | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 liter |
| Stabilizing solution | |
| Formalin | 2.0 ml |
| Water to make | 1 liter |

TABLE 2

| Photographic Material No. | Surface-Active Agent | Turbidity Ratio | Maximum Color Density | Remarks |
| --- | --- | --- | --- | --- |
| 401 | PW-3  | 1.807 | 1.57 | This Invention |
| 402 | PW-6  | 1.870 | 1.68 | " |
| 403 | PW-4  | 1.842 | 1.64 | " |
| 404 | PW-11 | 1.911 | 1.66 | " |
| 405 | PW-14 | 1.801 | 1.62 | " |
| 406 | SDDP* | 1.527 | 1.48 | Comparative Example |

Note; *SDDP: Sodium didodecylphosphate

As is apparent from the results in Table 2, in the case of emulsifying coupler C-2, the surface-active agents of the present invention can disperse the coupler finely, and when they are applied to photographic materials, the effect that the maximum color density is increased is remarkable.

EXAMPLE 5

Dispersion of Nucleator

Thirty mg of the below-mentioned nucleator used in photographic materials for G/A, and 30 mg of the surface-active agent shown in Table 3, were weighed and placed in a test tube, then after 2 ml of ethanol and 1 ml of water were added to dissolve them, 7 ml of water was added, all at once, to cause deposition. The dispersion obtained by the mixing and deposition was allowed to stand, and after about 1 hour, and after 1 day, the state of the dispersion was observed. By the visual evaluation from the side of the test tube, the state of the dispersion was evaluated with the below-mentioned three ratings: ○ (good; no precipitate being formed), Δ (somewhat good; precipitates slightly being formed on the bottom, but upper phase being dispersed), and x (bad: almost or perfectly being precipitated).

Results are shown in Table 3.

TABLE 3

Nucleator:

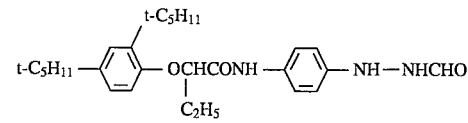

| Surface-active Agent | Dispersion State after One Hour | Dispersion State after one Day |
| --- | --- | --- |
| Sodium Dididecyl-phosphate | Δ (Upper phase being turbid, but precipitates being formed on the bottom) | x (Almost being precipitated) |
| Sodium Dodecyl-sulfate | Δ (Upper phase being turbid, but precipitates being formed on the bottom) | x (Perfectly being precipitated and upper phase being transparent) |
| PW-6 | ○ (Whole being uniformly turbid & dispersed, and no precipitate being formed) | ○ (Whole being uniformly turbid & dispersed, and no precipitate being formed) |
| PW-21 | ○ (Being remarkably turbid, and no precipitate being formed) | Δ (Precipitates slightly being formed on the bottom, but its upper phase being dispersed) |
| PW-31 | ○ (Being remarkably turbid, and no precipitate being | Δ (Precipitates slightly being formed on the bottom, but its upper |

TABLE 3-continued

Nucleator:

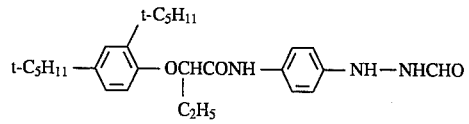

| Surface-active Agent | Dispersion State after One Hour | Dispersion State after one Day |
|---|---|---|
| | formed) | phase being dispersed) |

As is apparent from the results in Table 3, it can be understood that, while with conventionally known typical surface-active agents, precipitate takes place, with the surface-active agents of the present invention, the dispersion stability is excellent.

EXAMPLE 6

Layers described in Japanese Patent Application No. 208632/1992, pages 29 to 36, were applied successively on a triacetyl cellulose film support having an undercoat, to prepare Sample 601, which is a multi-layer color photographic material.

As a compound of the present invention, Compound PW-6 was used, in an amount of about 4 to 5% by weight to the coupler or hydrophobic hydroquinone in each layer, and each emulsion was prepared in accordance with the formulation in Example 1 and was used for each layer, as shown in Table 4.

TABLE 4

| Layer | Coating amount of PW-6 (g/m$^2$) |
|---|---|
| First Layer | 0.009 |
| Second Layer | 0.020 |
| Third Layer | 0.013 |
| Fourth Layer | 0.015 |
| Fifth Layer | 0.010 |
| Sixth Layer | — |
| Seventh Layer | 0.006 |
| Eighth Layer | 0.002 |
| Ninth Layer | 0.007 |
| Tenth Layer | — |
| Eleventh Layer | 0.033 |
| Twelfth Layer | 0.006 |
| Thirteenth Layer | 0.001 |
| Fourteenth Layer | 0.015 |
| Fifteenth Layer | — |

The thus-prepared color photographic material was subjected, after exposure to light, to the processing described below (until the accumulated replenisher amount of developer reached to three times the volume of tank), using an automatic processor.

(Processing process)

| Processing step | Time | Temperature | Replenisher* | Tank Volume |
|---|---|---|---|---|
| Color developing | 3 min 15 sec | 38° C. | 22 ml | 20 liter |
| Bleaching | 3 min 00 sec | 38° C. | 25 ml | 40 liter |
| Washing (1) | 15 sec | 24° C. | Countercurrent piping mode from (2) to (1) 10 liter | |
| Washing (2) | 15 sec | 24° C. | 15 ml | 10 liter |
| Fixing | 3 min 00 sec | 38° C. | 15 ml | 30 liter |
| Washing (3) | 30 sec | 24° C. | Countercurrent piping mode from (4) to (3) 10 liter | |
| Washing (4) | 30 sec | 24° C. | 1,200 ml | 10 liter |
| Stabilizing | 30 sec | 38° C. | 20 ml | 10 liter |
| Drying | 4 min 20 sec | 55° C. | | |

Note:
*Replenisher amount per one meter length of 35 mm width.

The composition of each processing solution is shown below.

| Color-developer | Tank Solution (g) | Replenisher (g) |
|---|---|---|
| Diethylenetriaminepentaacetic acid | 1.0 | 1.2 |
| 1-hydroxyethylidene-1,1-diphosphonic acid | 2.0 | 2.2 |
| Sodium sulfite | 4.0 | 4.8 |
| Potassium carbonate | 30.0 | 39.0 |
| Potassium bromide | 1.4 | 0.3 |
| Potassium iodide | 1.5 mg | — |
| Hydroxylamine sulfate | 2.4 | 3.1 |
| 4-[N-Ethyl-N(β-hydroxyethyl)amino]-2-methylaniline sulfate | 4.5 | 6.0 |
| Water to make | 1.0 liter | 1.0 liter |
| pH (adjusted by potassium hydroxide and sulfuric acid) | 10.05 | 10.15 |

| Bleaching solution | Tank Solution (g) | Replenisher (g) |
|---|---|---|
| Iron (II)sodium ethylenediaminetetraacetate trihydrate | 100.0 | 120.0 |
| Disodium ethylenediaminetetraacetate | 10.0 | 11.0 |
| 3-Mercapto-1,2,4-triazole | 0.03 | 0.08 |
| Ammonium bromide | 140.0 | 160.0 |
| Ammonium nitrate | 30.0 | 35.0 |
| Aqueous ammonia (27%) | 6.5 ml | 4.0 ml |
| Water to make | 1.0 liter | 1.0 liter |
| pH (adjusted by aqueous ammonia and nitric acid) | 6.0 | 5.7 |

| Fixing solution | Tank Solution (g) | Replenisher (g) |
|---|---|---|
| Disodium ethylenediaminetetraacetate | 0.5 | 0.7 |
| Ammonium sulfite | 20.0 | 22.0 |
| Aqueous ammonium thiosulfite solution (700 g/liter) | 295.0 ml | 320.0 ml |
| Acetic acid (90%) | 3.3 | 4.0 |
| Water to make | 1.0 liter | 1.0 liter |
| pH (adjusted by aqueous ammonia and acetic acid) | 6.7 | 6.8 |

| Stabilizing solution (Both tank solution and replenisher are the same) (g) | |
|---|---|
| Sodium p-toluenesulphinate | 0.03 |
| Polyoxyethylene-p-monononylphenyl ether (average polymerization degree: 10) | 0.2 |
| Disodium ethylenediaminetetraacetate | 0.05 |
| 1,2,4-triazole | 1.3 |
| 1,4-bis(1,2,4-triazole-1-ylmethyl)piperazine | 0.75 |
| Water to make | 1.0 liter |
| pH | 8.5 |

By the above processing, a sample excellent in gradation, color reproduction, and color-forming properties was obtained.

Having described our invention as related to the present embodiments, it is our intention that the invention not be limited by any of the details of the description, unless otherwise specified, but rather be construed broadly within its spirit and scope as set out in the accompanying claims.

What we claim is:

1. A silver halide photographic material, which comprises a light-sensitive silver halide and a compound represented by the following formula (I):

   formula (I)

wherein $R_1$ represents an aliphatic group, an alicyclic compound group, an aromatic group, or a heterocyclic ring; $R_2$ represents an aliphatic group, an alicyclic compound group, an aromatic group, e. heterocyclic ring, or a group represented by —L—Z; $Q_1$, $Q_2$, and $Q_3$ each represent a single bond, an oxygen atom, a sulfur atom, or a group represented by —N($R_3$)—, in which $R_3$ represents a hydrogen atom or a group represented by $R_2$; L represents a divalent linking group; and Z represents an ionic group.

2. The silver halide photographic material as claimed in claim 1, wherein $R_1$ in formula (I) is selected from the group consisting of a straight-chain or branched alkyl group, a straight-chain or branched alkenyl group, a straight-chain or branched alkynyl group, a cycloalkyl group, a cycloalkenyl group, an aryl group, a cyclic ether, and a nitrogen-containing ring.

3. The silver halide photographic material as claimed in claim 1, wherein $R_2$ in formula (I) is selected from the group consisting of a straight-chain or branched alkyl group, a straight-chain or branched alkenyl group, a straight-chain or branched alkynyl group, a cycloalkyl group, a cycloalkenyl group, an aryl group, a cyclic ether, a nitrogen-containing ring, and a group represented by —L—Z, wherein L is a group represented by the following formula (III):

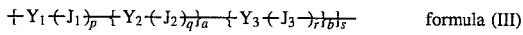   formula (III)

wherein $Y_1$, $Y_2$, and $Y_3$, which are the same or different, each represent an alkylene group or an arylene group; $J_1$, $J_2$, and $J_3$, which are the same or different, each represent a divalent linking unit; p, q, and r are each independently an integer of 0 to 5; a and b are each independently an integer of 0 to 50; s is an integer of from 1 to 10; and Z is a hydrophilic anionic group or a hydrophilic cationic group.

4. The silver halide photographic material as claimed in claim 1, wherein L in formula (I) is a group represented by the following formula (III):

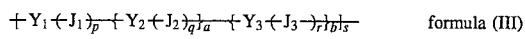   formula (III)

wherein $Y_1$, $Y_2$, and $Y_3$, which are the same or different, each represent an alkylene group or an arylene group; $J_1$, $J_2$, and $J_3$, which are the same or different, each represent a divalent linking unit; p, q, and r are each independently an integer of 0 to 5; a and b are each independently an integer of 0 to 50; and s is an integer of from 1 to 10.

5. The silver halide photographic material as claimed in claim 1, wherein Z in formula (I) is a hydrophilic anionic group or a hydrophilic cationic group.

6. The silver halide photographic material as claimed in claim 1, wherein the compound represented by formula (I) is used as a dispersant for a hydrophobic photographically useful compound.

7. The silver halide photographic material as claimed in claim 6, wherein the hydrophobic photographically useful compound is an organic or inorganic compound that is useful photographically.

8. The silver halide photographic material as claimed in claim 1, wherein the compound represented by formula (I) is incorporated into at least one layer of the photographic material.

9. The silver halide photographic material as claimed in claim 1, wherein the amount to be used of the compound represented by formula (I) is 0.0001 to 1 g/m² as the total amount in the photographic material.

10. The silver halide photographic material as claimed in claim 1, wherein Z in formula (I) is —$SO_3M$ or —$OSO_3M$, in which M represents a counter cation.

11. The silver halide photographic material as claimed in claim 2, wherein said alkyl group, alkenyl group, alkynyl group, cycloalkyl group, cycloalkenyl group, aryl group, cyclic ether, and nitrogen-containing ring are unsubstituted.

12. The silver halide photographic material as claimed in claim 3, wherein said alkyl group, alkenyl group, alkynyl group, cycloalkyl group, cycloalkenyl group, aryl group, cyclic ether, nitrogen-containing ring, alkylene group, and arylene group are unsubstituted.

13. The silver halide photographic material as claimed in claim 4, wherein said alkylene group and arylene group are unsubstituted.

* * * * *